(12) United States Patent
Buyda et al.

(10) Patent No.: US 12,334,665 B2
(45) Date of Patent: Jun. 17, 2025

(54) SURGICAL INSTRUMENT WITH ELECTRICAL CONNECTION

(71) Applicant: Covidien LP, Mansfield, MA (US)

(72) Inventors: Andriy Buyda, Northford, CT (US);
David M. Chowaniec, Rocky Hill, CT (US); Xingrui Chen, Glastonbury, CT (US); Brian J. Creston, Madison, CT (US); Saumya Banerjee, Southington, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/539,557

(22) Filed: Dec. 14, 2023

(65) Prior Publication Data

US 2024/0113462 A1   Apr. 4, 2024

Related U.S. Application Data

(63) Continuation of application No. 17/402,772, filed on Aug. 16, 2021, now Pat. No. 11,862,884.

(51) Int. Cl.
*A61B 17/072* (2006.01)
*H01R 13/24* (2006.01)
(Continued)

(52) U.S. Cl.
CPC ....... *H01R 13/2442* (2013.01); *A61B 17/072* (2013.01); *A61B 17/07207* (2013.01);
(Continued)

(58) Field of Classification Search
CPC . A61B 17/068; A61B 17/0684; A61B 17/072; A61B 17/07207; A61B 17/115;
(Continued)

(56) References Cited

U.S. PATENT DOCUMENTS 2,957,353 A   10/1960 Babacz
3,111,328 A   11/1963 Di Rito et al.
(Continued)

FOREIGN PATENT DOCUMENTS

CA   2451558 A1   1/2003
CN   102247182 A   11/2011
(Continued)

OTHER PUBLICATIONS

International Search Report and Written Opinion dated Nov. 9, 2022, issued in corresponding international application No. PCT/IB2022/057375, 17 pages.

*Primary Examiner* — Scott A Smith (57) ABSTRACT

A surgical instrument includes a housing, an elongated portion, and a loading unit. The elongated portion extends distally from the housing, defines a longitudinal axis, and includes an electrical contact. The loading unit is configured to releasably engage the elongated portion. The loading unit includes an electronic component, a proximal portion including an electrical contact in electrical communication with the electronic component, and an end effector coupled to the proximal portion and configured to manipulate tissue. Engagement between the elongated portion and the loading unit causes the electrical contact of the elongated portion to engage the electrical contact of the loading unit thereby electrically connecting the elongated portion and the loading unit.

20 Claims, 4 Drawing Sheets

(51) Int. Cl.
  *A61B 17/00* (2006.01)
  *A61B 17/068* (2006.01)
  *A61B 17/115* (2006.01)
  *A61B 34/30* (2016.01)

(52) U.S. Cl.
  CPC ... *A61B 2017/00477* (2013.01); *A61B 17/068* (2013.01); *A61B 2017/07214* (2013.01); *A61B 17/115* (2013.01); *A61B 34/30* (2016.02); *H01R 2201/12* (2013.01)

(58) Field of Classification Search
  CPC .......... A61B 2017/07214; A61B 2017/07271; A61B 2017/00477; A61B 2017/2929; A61B 34/30; A61B 90/03; A61B 90/06; A61B 90/08
  USPC ..... 227/19, 175.1, 175.2, 176.1; 606/1, 139, 606/219
  See application file for complete search history.

(56) References Cited

U.S. PATENT DOCUMENTS

| | | |
|---|---|---|
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,504,227 A | 3/1985 | Lohn |
| 4,606,343 A | 8/1986 | Conta et al. |
| 4,705,038 A | 11/1987 | Sjostrom et al. |
| 4,722,685 A | 2/1988 | de Estrada et al. |
| 4,810,139 A | 3/1989 | Regan |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,632,432 A | 5/1997 | Schulze et al. |
| 5,647,526 A | 7/1997 | Green et al. |
| 5,653,374 A | 8/1997 | Young et al. |
| 5,658,300 A | 8/1997 | Bito et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | Mckean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | Mckean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,899,538 B2 | 5/2005 | Matoba |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,328,828 B2 | 2/2008 | Ortiz et al. |
| 7,364,061 B2 | 4/2008 | Swayze et al. |

(56) References Cited

U.S. PATENT DOCUMENTS

| | | |
|---|---|---|
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,819,896 B2 | 10/2010 | Racenet |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,551,076 B2 | 10/2013 | Duval et al. |
| 8,561,871 B2 | 10/2013 | Rajappa et al. |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,758,391 B2 | 6/2014 | Swayze et al. |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,597,104 B2 | 3/2017 | Nicholas et al. |
| 9,839,425 B2 | 12/2017 | Zergiebel et al. |
| 10,548,595 B2 | 2/2020 | Zergiebel et al. |
| 10,973,514 B2 | 4/2021 | Zergiebel et al. |
| 11,862,884 B2 | 1/2024 | Buyda et al. |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0176751 A1 | 9/2004 | Weitzner et al. |
| 2004/0193146 A1 | 9/2004 | Lee et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2008/0029570 A1 | 2/2008 | Shelton et al. |

(56) References Cited

U.S. PATENT DOCUMENTS

| | | |
|---|---|---|
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0118315 A1 | 5/2008 | Brunson |
| 2008/0146353 A1 | 6/2008 | Boffelli et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0194954 A1 | 8/2009 | Hsu |
| 2009/0209990 A1 | 8/2009 | Yates et al. |
| 2009/0254094 A1 | 10/2009 | Knapp et al. |
| 2009/0261539 A1 | 10/2009 | Paulsen |
| 2009/0273146 A1 | 11/2009 | Dezheng et al. |
| 2009/0314821 A1 | 12/2009 | Racenet |
| 2010/0056986 A1 | 3/2010 | Allen et al. |
| 2010/0069942 A1 | 3/2010 | Shelton, IV |
| 2010/0081108 A1 | 4/2010 | Webster |
| 2010/0089974 A1 | 4/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1 | 7/2011 | Ross et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0083783 A1* | 4/2012 | Davison ............ A61B 18/1445 606/45 |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0018361 A1 | 1/2013 | Bryant |
| 2013/0093149 A1 | 4/2013 | Saur et al. |
| 2013/0181035 A1 | 7/2013 | Milliman |
| 2013/0184704 A1 | 7/2013 | Beardsley et al. |
| 2013/0211397 A1 | 8/2013 | Parihar et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236173 A1 | 8/2014 | Scirica et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0148829 A1 | 5/2015 | Kimball |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0216525 A1 | 8/2015 | Collins et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0174972 A1 | 6/2016 | Shelton, IV |
| 2018/0168622 A1 | 6/2018 | Shelton, IV |
| 2019/0000464 A1 | 1/2019 | Shelton, IV |
| 2019/0000476 A1 | 1/2019 | Shelton, IV |
| 2019/0000525 A1 | 1/2019 | Messerly |
| 2019/0183493 A1 | 6/2019 | Shelton, IV |
| 2019/0183503 A1 | 6/2019 | Shelton, IV et al. |
| 2019/0290271 A1 | 9/2019 | Scott |
| 2019/0290307 A1 | 9/2019 | Posey |
| 2019/0290308 A1 | 9/2019 | Worthington |
| 2020/0261089 A1 | 8/2020 | Shelton, IV et al. |

FOREIGN PATENT DOCUMENTS

| | | |
|---|---|---|
| DE | 102008053842 A1 | 5/2010 |
| EP | 0634144 A1 | 1/1995 |
| EP | 0648476 A1 | 4/1995 |
| EP | 0686374 A2 | 12/1995 |
| EP | 0705571 A1 | 4/1996 |
| EP | 1690502 A1 | 8/2006 |
| EP | 1723913 A1 | 11/2006 |
| EP | 1736112 A1 | 12/2006 |
| EP | 1769754 A1 | 4/2007 |
| EP | 1772105 A1 | 4/2007 |
| EP | 1813199 A1 | 8/2007 |
| EP | 1813203 A2 | 8/2007 |
| EP | 1813211 A2 | 8/2007 |
| EP | 1943954 A2 | 7/2008 |
| EP | 1943956 A2 | 7/2008 |
| EP | 1943958 A1 | 7/2008 |

(56) References Cited

FOREIGN PATENT DOCUMENTS

| | | | |
|---|---|---|---|
| EP | 1943976 | A2 | 7/2008 |
| EP | 2005898 | A2 | 12/2008 |
| EP | 2027819 | A1 | 2/2009 |
| EP | 2044890 | A1 | 4/2009 |
| EP | 2055243 | A2 | 5/2009 |
| EP | 2098170 | A2 | 9/2009 |
| EP | 2100561 | A2 | 9/2009 |
| EP | 2100562 | A2 | 9/2009 |
| EP | 2165664 | A2 | 3/2010 |
| EP | 2236098 | A2 | 10/2010 |
| EP | 2263568 | A2 | 12/2010 |
| EP | 2272443 | A1 | 1/2011 |
| EP | 2316345 | A1 | 5/2011 |
| EP | 2324776 | A2 | 5/2011 |
| EP | 2329773 | A1 | 6/2011 |
| EP | 2333509 | A1 | 6/2011 |
| EP | 2462878 | A1 | 6/2012 |
| EP | 2462880 | B1 | 6/2012 |
| EP | 2491872 | A1 | 8/2012 |
| EP | 2586382 | A2 | 5/2013 |
| EP | 2606834 | A2 | 6/2013 |
| EP | 2668910 | A2 | 12/2013 |
| EP | 2676615 | A2 | 12/2013 |
| EP | 2839786 | A1 | 2/2015 |
| EP | 2881046 | A2 | 6/2015 |
| EP | 3549545 | A2 | 10/2019 |
| EP | 3586767 | A2 | 1/2020 |
| EP | 3922193 | A1 | 12/2021 |
| ES | 2333509 | A1 | 2/2010 |
| JP | 08038488 | | 2/1996 |
| JP | 2005125075 | A | 5/2005 |
| KR | 20120022521 | A | 3/2012 |
| WO | 9915086 | A1 | 4/1999 |
| WO | 0072760 | A1 | 12/2000 |
| WO | 0072765 | A1 | 12/2000 |
| WO | 03000138 | A2 | 1/2003 |
| WO | 03026511 | A1 | 4/2003 |
| WO | 03030743 | A2 | 4/2003 |
| WO | 03065916 | A1 | 8/2003 |
| WO | 03077769 | A1 | 9/2003 |
| WO | 03090630 | A2 | 11/2003 |
| WO | 2004107989 | A1 | 12/2004 |
| WO | 2006042210 | A2 | 4/2006 |
| WO | 2007016290 | A2 | 2/2007 |
| WO | 2007026354 | A1 | 3/2007 |
| WO | 2007137304 | A2 | 11/2007 |
| WO | 2008131362 | A2 | 10/2008 |
| WO | 2008133956 | A2 | 11/2008 |
| WO | 2009039506 | A1 | 3/2009 |
| WO | 2007014355 | A3 | 4/2009 |
| WO | 2009132359 | A2 | 10/2009 |
| WO | 2009143092 | A1 | 11/2009 |
| WO | 2009149234 | A1 | 12/2009 |
| WO | 2011108840 | A2 | 9/2011 |
| WO | 2012040984 | A1 | 4/2012 |

\* cited by examiner

FIG. 4 under construction...

SURGICAL INSTRUMENT WITH ELECTRICAL CONNECTION

CROSS-REFERENCE TO RELATED APPLICATIONS

This application is a continuation of U.S. patent application Ser. No. 17/402,772, filed Aug. 16, 2021, now U.S. Pat. No. 11,862,884, the entire disclosure of which is incorporated by reference herein.

BACKGROUND

Technical Field

The present disclosure relates generally to instruments for surgically manipulating tissue and, more specifically, to surgical instruments that form an electrical connection with a loading unit.

Background of Related Art

Various types of surgical instruments used to surgically manipulate and join tissue are known in the art, and are commonly used, for example, for closure of tissue or organs in transection, resection, anastomoses, for occlusion of organs in thoracic and abdominal procedures, and for electrosurgically fusing or sealing tissue.

Surgical instruments may be operated manually, robotically, with powered components, or any combination thereof.

Additionally, a loading unit (e.g., a single use loading unit or a disposable loading unit) may be attached to an elongated or endoscopic portion of several types of surgical instruments. Such loading units allow surgical instruments to have greater versatility, for example. The loading units may be configured for a single use, and/or may be configured for multiple uses.

Further, some loading units include an identification chip and/or other electronic components. When such a loading unit is used with the remainder of the surgical instrument (e.g., when the loading unit having an identification chip is engaged with an elongated portion of a surgical instrument), it may be important to relay the information included on the identification chip of the loading unit to the surgical instrument engaged therewith. Thus, it may be suitable to provide a surgical instrument that can provide an electrical connection with a loading unit engaged therewith.

SUMMARY

The disclosure relates to a surgical instrument comprising a housing, an elongated portion, and a loading unit. The elongated portion extends from the housing, defines a longitudinal axis, and includes an electrical contact. The loading unit is configured to releasably engage the elongated portion. The loading unit includes an electronic component, a proximal portion including an electrical contact in electrical communication with the electronic component, and an end effector coupled to the proximal portion and configured to manipulate tissue. Engagement between the elongated portion and the loading unit causes the electrical contact of the elongated portion to engage the electrical contact of the loading unit thereby electrically connecting the elongated portion and the loading unit.

In aspects, the electrical contact of the elongated portion may be movable toward and away from the longitudinal axis.

In aspects, the electrical contact of the elongated portion may include at least five linear segments. In disclosed aspects, three linear segments of the five linear segments of the electrical contact of the elongated portion may form a flat-bottom V-shape. In further disclosed aspects, the electrical contact of the elongated portion may be made from sheet metal.

In aspects, the electrical contact of the loading unit may be movable toward and away from the longitudinal axis.

In aspects, a distal end of the electrical contact of the loading unit may be fixed from movement relative to the longitudinal axis, and a proximal end of the electrical contact of the loading unit may be movable toward and any from the longitudinal axis.

In aspects, a proximal end of the electrical contact of the loading unit may form an acute angle with the longitudinal axis.

The disclose also relates to a surgical instrument configured to releasably engage a loading unit having an electronic component. The surgical instrument comprises a powered handle assembly, an elongated portion, and an electrical contact. The elongated portion extends distally from the powered handle assembly, defines a longitudinal axis, and includes an outer wall. The electrical contact is disposed within the outer wall of the elongated portion. At least a portion of the electrical contact is movable toward and away from the longitudinal axis. The electrical contact is configured to communicate with the electronic component of the loading unit when the surgical instrument is engaged with the loading unit.

In aspects, the electrical contact may include at least five linear segments. In disclosed aspects, three linear segments of the five linear segments of the electrical contact may form a flat-bottom V-shape. In further disclosed aspects, the electrical contact may be made from sheet metal.

In aspects, the surgical instrument may include at least one of a processor or a storage unit disposed in electrical communication with the electrical contact.

BRIEF DESCRIPTION OF THE DRAWINGS

Various embodiments of the disclosure are illustrated herein with reference to the accompanying drawings, wherein.

DETAILED DESCRIPTION

Embodiments of the disclosed surgical instrument are described in detail with reference to the drawings, wherein like reference numerals designate corresponding elements in each of the several views. As is common in the art, the term "proximal" refers to that part or component closer to the user or operator, e.g., surgeon or physician, while the term "distal" refers to that part or component farther away from the user.

FIGS. 1-6 illustrate a surgical instrument in accordance with an aspect of the disclosure generally designated as reference numeral 100. While the surgical instrument 100 in the accompanying figures is depicted as a surgical stapling instrument, the surgical instrument 100 of the disclosure is not limited to a surgical stapling instrument; the surgical instrument 100 may be any suitable surgical instrument including but not limited to a vessel sealing instrument, a surgical grasper, a surgical clip applier, a circular stapling instrument, etc.

Figure 1:
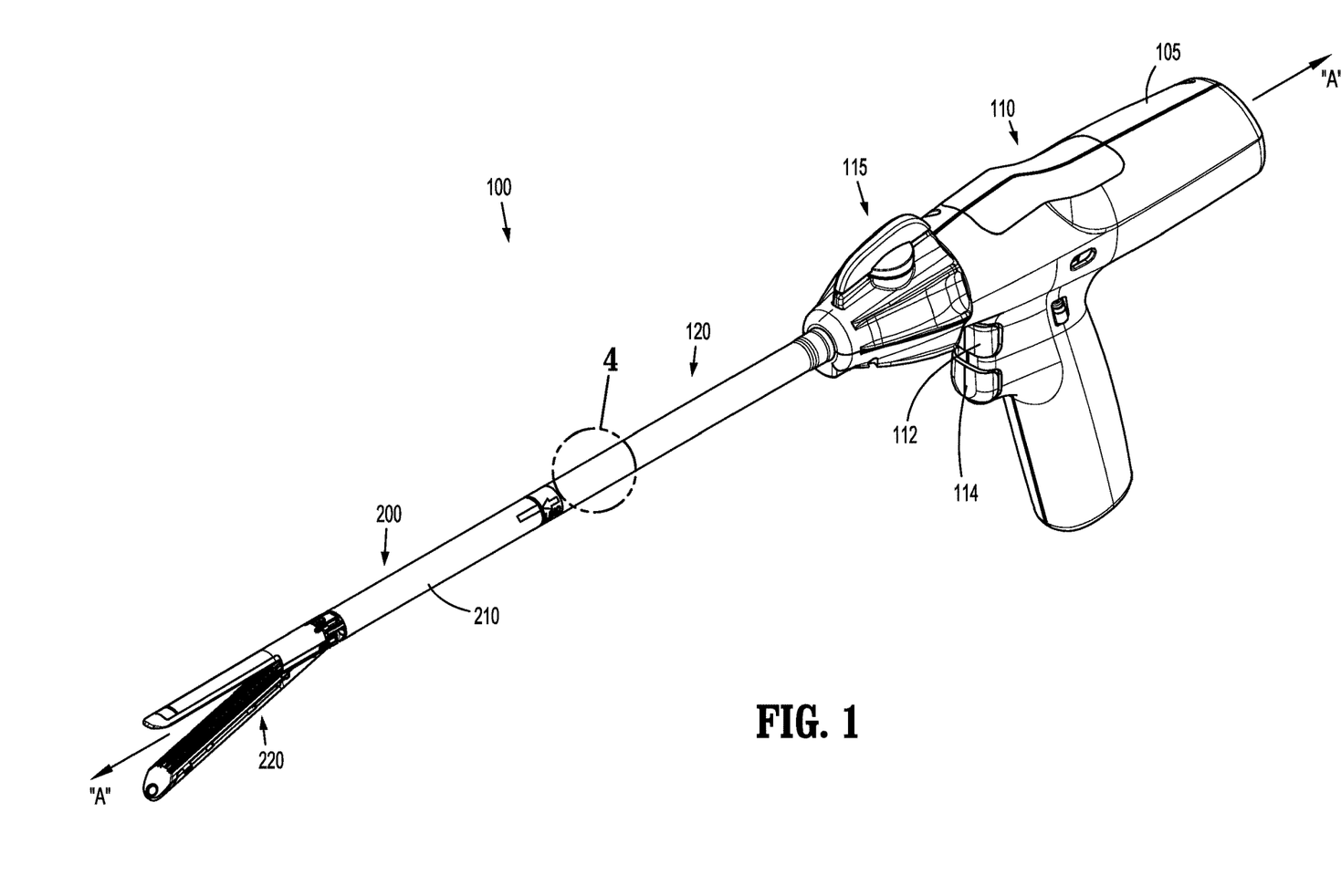
FIG. 1 is a perspective view of a surgical instrument in accordance with an embodiment of the disclosure.

With particular reference to FIG. 1, the surgical instrument 100 includes a housing 105, a handle assembly 110, an adapter assembly 115, an elongated portion 120 extending distally from the adapter assembly 115 and defining a longitudinal axis "A-A," and a loading unit 200 engaged with a distal end of the elongated portion 120. The loading unit 200 includes a proximal portion 210 and an end effector 220, and is releasably engageable with the elongated portion 120. While FIG. 1 illustrates the surgical instrument 100 including a powered handle assembly including a first actuator 112 and a second actuator 114, other types of handles can be used such as, for example, those including a pivotable handle, motor-driven, hydraulic, ratcheting, etc. As used herein, "handle assembly" encompasses all types of handle assemblies. Additionally, the surgical instrument 100 and components thereof are usable as part of a robotic surgical system.

Figure 2:
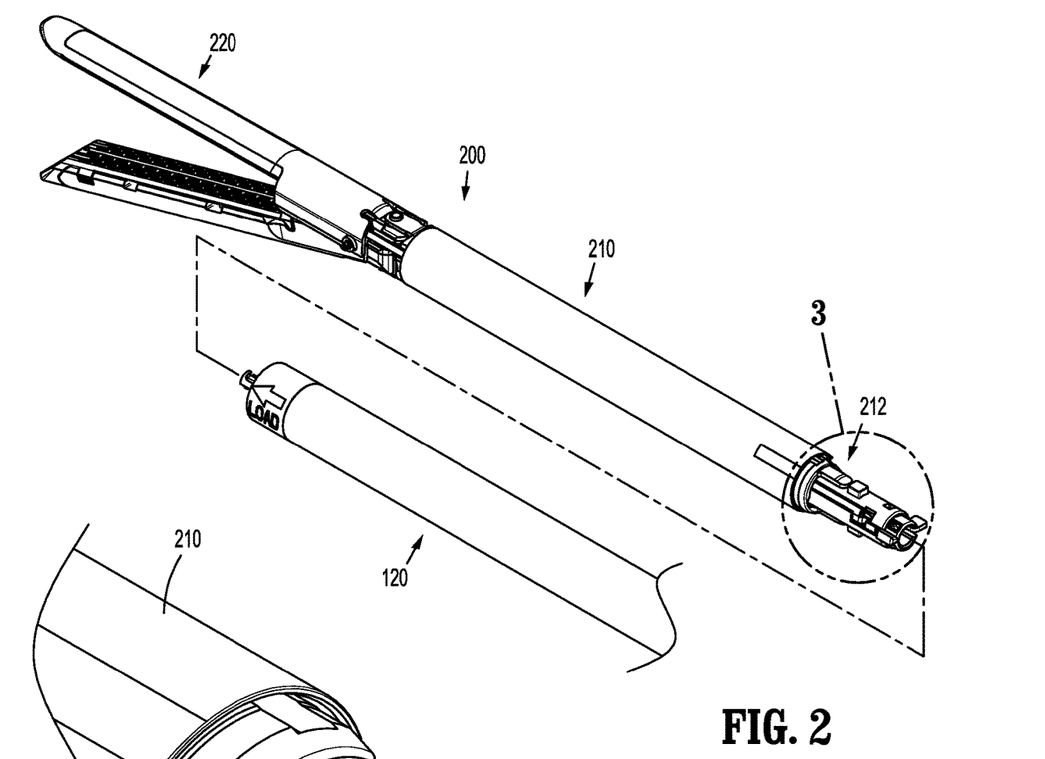
FIG. 2 is a perspective, assembly view of the surgical instrument of FIG. 1 illustrating a loading unit and part of an elongated portion.
Figure 3:
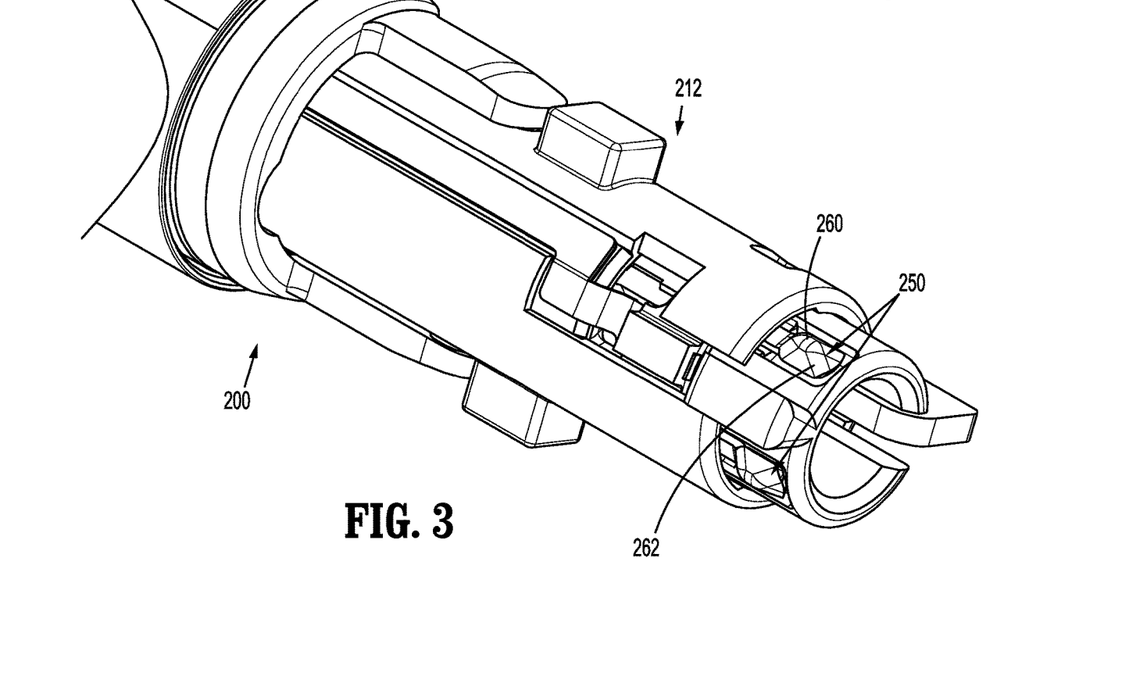
FIG. 3 is an enlarged view of the area of detail indicated in FIG. 2, showing a proximal portion of the loading unit.

Referring now to FIGS. 2 and 3, details of the loading unit 200 are shown. The proximal portion 210 of the loading unit 200 includes a plurality of electrical contacts 250 adjacent a proximal end 212 thereof. Each electrical contact of the plurality of electrical contacts 250 is configured to store and relay information, and may either include or be in electrical communication with an electronic component 270 via leads 272, for instance (shown schematically in FIG. 4). The electronic component 270 may be a storage device, such as an EPROM or any suitable flash storage device, configured to store information relating to the type of end effector 220 (e.g., used for surgical stapling, vessel sealing, etc.) included on the loading unit 200, the length of the loading unit 200, the diameter of the loading unit 200, the number of fasteners included within the end effector 220, etc. In aspects, the electronic component 270 may be a sensor or an actuator.

Figure 4:
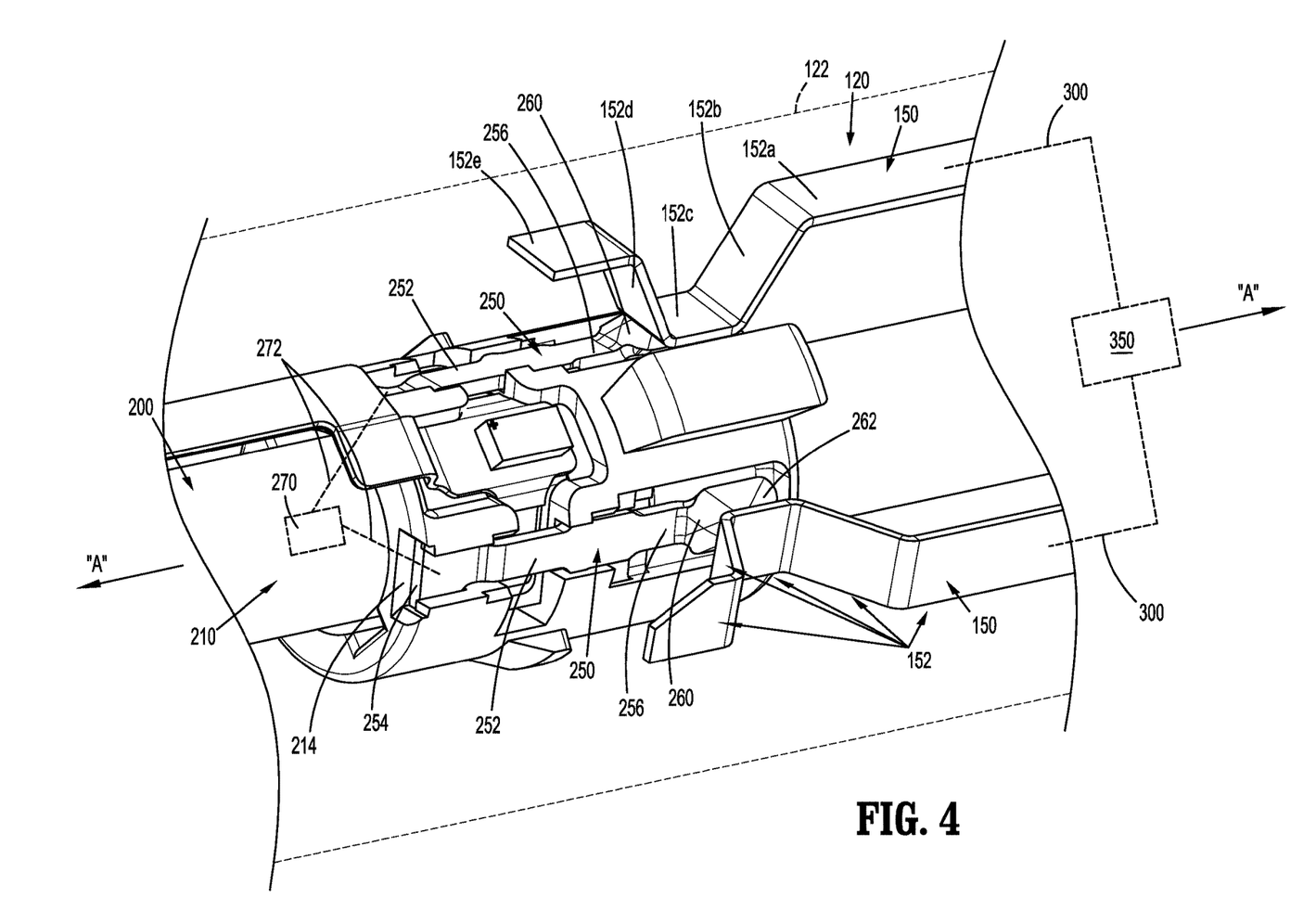
FIG. 4 is an enlarged view illustrating distal portions of the elongated portion engaged with proximal portions of the loading unit of the surgical instrument within the area of detail indicated in FIG. 1.

With reference to FIG. 4, each electrical contact of the plurality of electrical contacts 250 includes an arm 252 and a finger 260. A distal end 254 of the arm 252 is engaged with a mounting portion 214 of the proximal portion 210 of the loading unit 200. The finger 260 of each electrical contact of the plurality of electrical contacts 250 extends proximally from a proximal end 256 of the arm 252. In this arrangement, the finger 260 and parts of the arm 252 of each electrical contact of the plurality of electrical contacts 250 are cantilevered thereby enabling portions of the plurality of electrical contacts 250 to flex toward and away from the longitudinal axis "A-A." In aspects, the structure of the plurality of electrical contacts 250 biases the plurality of electrical contacts 250 radially outward away from the longitudinal axis "A-A."

Figures 5, 6:
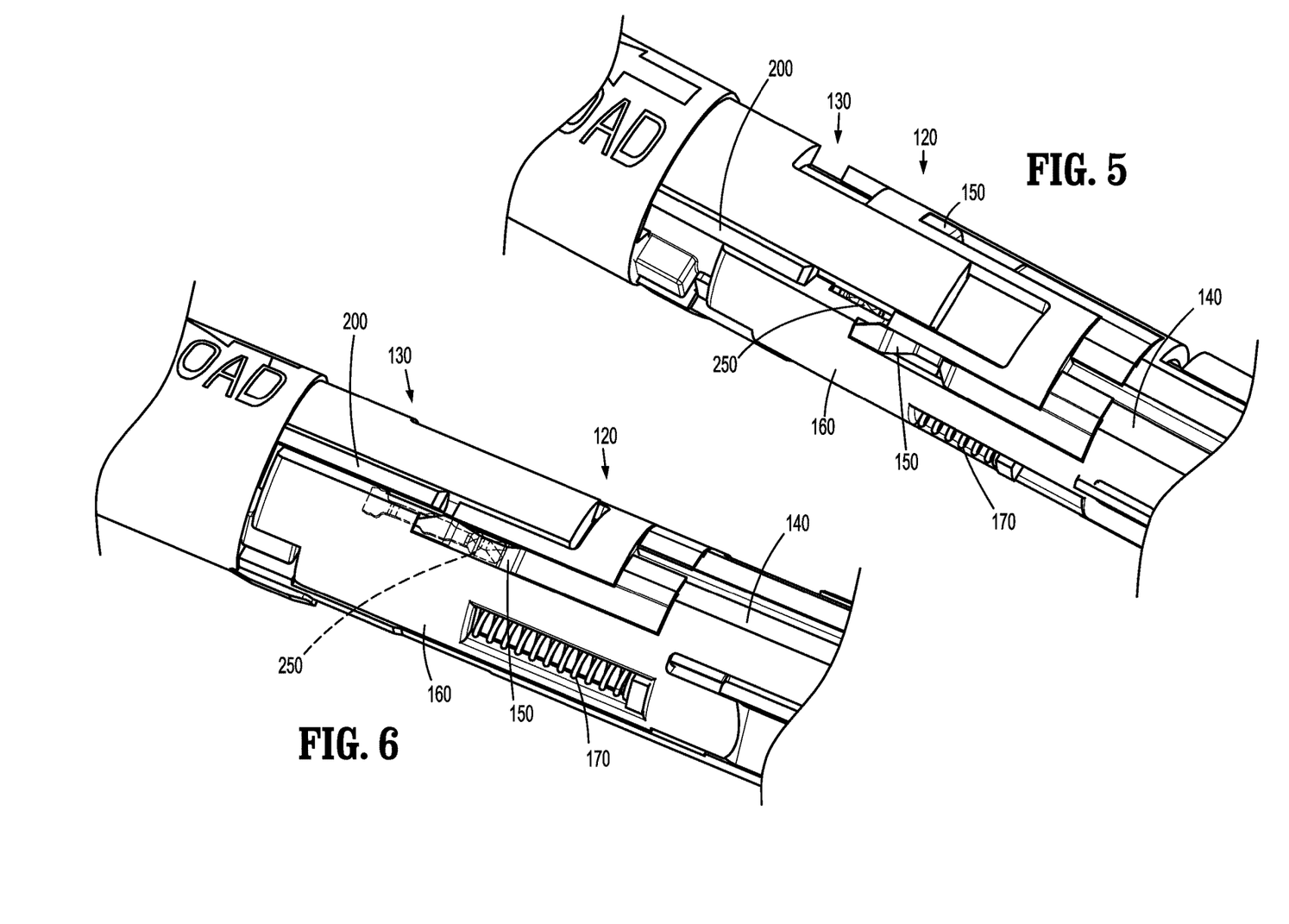
FIG. 5 is a perspective view illustrating portions of the loading unit and the elongated portion in a partially-engaged position.
FIG. 6 is a perspective view illustrating portions of the loading unit and the elongated portion in a fully-engaged position.

With particular reference to FIGS. 4-6, engagement between the loading unit 200 and the elongated portion 120 of the surgical instrument 100 is shown. For clarity, an outer wall 122 of the elongated portion 120 is shown in phantom in FIG. 4 and is omitted in FIGS. 5 and 6. The elongated portion 120 includes an engagement interface 130 that is configured to selectively engage portions of the loading unit 200. More particularly, the engagement interface 130 of the elongated portion 120 includes a base 140, a plurality of electrical contacts 150, a loading linkage 160, and a biasing element 170. In aspects, the number of electrical contacts of the plurality of electrical contacts 150 of the elongated portion 120 is equal to the number of electrical contacts of the plurality of electrical contacts 250 of the loading unit 200. In other aspects, the number of electrical contacts of the plurality of electrical contacts 150 of the elongated portion 120 is greater than or less than the number of electrical contacts of the plurality of electrical contacts 250 of the loading unit 200.

Referring to FIG. 4, each electrical contact of the plurality of electrical contacts 150 of the elongated portion 120 includes a plurality of segments 152. More particularly, in the illustrated aspect, each electrical contact of the plurality of electrical contacts 150 includes five segments 152: a first segment 152a, a second segment 152b, a third segment 152c, a fourth segment 152d, and a fifth segment 152e. Each electrical contact of the plurality of electrical contacts 150 may include more or fewer than five segments 152. Additionally, in the illustrated aspect, the first segment 152a, the third segment 152c, and the fifth segment 152e are parallel or generally parallel to each other and to the longitudinal axis "A-A," and the second segment 152b and the fourth segment 152d are disposed at angles relative to their adjoining segments such that the second segment 152b, the third segment 152c, and the fourth segment 152d form a flat-bottom V-shape. Further, in aspects, the plurality of electrical contacts 150 is made of sheet metal.

Upon engagement between the loading unit 200 and the elongated portion 120 of the surgical instrument 100, the plurality of electrical contacts 250 of the loading unit 200 are moved proximally relative to the plurality of electrical contacts 150 of the elongated portion 120. Upon initial engagement, and as shown in FIG. 5, the plurality of electrical contacts 250 of the loading unit 200 and the plurality of electrical contacts 150 of the elongated portion 120 are free from physical contact with each other.

Upon continued and full engagement, and as shown in FIGS. 4 and 6, the plurality of electrical contacts 250 of the loading unit 200 and the plurality of electrical contacts 150 of the elongated portion 120 are in physical contact with each other. More particularly, in this position, the third segment 152c of each electrical contact of the plurality of electrical contacts 150 of the elongated portion 120 is in physical contact with the finger 260 of one electrical contact of the plurality of electrical contacts 250 of the loading unit 200 (see FIG. 4). This engagement is facilitated by the angled fourth segment 152d of the plurality of electrical contacts 150 of the elongated portion 120, by a ramped proximal portion 262 of the finger 260 of the plurality of electrical contacts 250 of the loading unit 200, and by the ability of both the plurality of electrical contacts 150 of the elongated portion 120 and the plurality of electrical contacts 250 of the loading unit 200 to be able to flex relative to the longitudinal axis "A-A," for instance.

With reference to FIGS. 5 and 6, the base 140, the loading linkage 160, and the biasing element 170 are shown. FIG. 5 illustrates initial engagement between the loading unit 200 and the elongated portion 120. Here, the loading linkage 160 is in a proximal position relative to the base 140. In aspects, a portion of the base 140 may physically contact a portion of the loading linkage 160 to resist the distally-directed force of the biasing element 170. Additionally, as discussed above, in this initial engagement, the plurality of electrical contacts 150 of the elongated portion 120 are not in physical contact with the plurality of electrical contacts 250 of the loading unit 200.

FIG. 6 illustrates complete engagement between the loading unit 200 and the elongated portion 120. Here, the biasing element 170 has urged the loading linkage 160 to its distal position relative to the base 140. Moreover, as discussed above, in this complete or full engagement, each electrical contact of the plurality of electrical contacts 150 of the elongated portion 120 is in physical contact with one electrical contact of the plurality of electrical contacts 250 of the loading unit 200.

Additionally, upon proper engagement, the information stored on the plurality of electrical contacts 250 and/or the electronic component 270 of the loading unit 200 is electrically communicated through the plurality of electrical contacts 150 of the elongated portion 120, and through leads 300 (schematically illustrated in FIG. 4), to a processor and/or storage unit 350 (schematically illustrated in FIG. 4) which is engaged with the elongated portion 120, the housing 105, the handle assembly 110, and/or the adapter assembly 115, thereby allowing the surgical instrument 100 to receive the information stored on the loading unit 200.

While the above description contains many specifics, these specifics should not be construed as limitations on the scope of the present disclosure, but merely as illustrations of various embodiments thereof. Therefore, the above description should not be construed as limiting, but merely as exemplifications of various aspects. Those skilled in the art will envision other modifications within the scope and spirit of the claims appended hereto.

What is claimed is:

1. A surgical instrument configured to releasably engage a loading unit having an electronic component, the surgical instrument comprising:
   a powered assembly;
   an elongated portion coupled to the powered assembly, defining a central longitudinal axis, and including an outer wall; and
   an electrical contact disposed within the outer wall of the elongated portion, at least a portion of the electrical contact being movable radially inward and outward relative to the central longitudinal axis, the electrical contact having at least three segments including a first segment, a second segment, and a third segment, the second segment disposed distally of and radially inward from the first segment, and the third segment disposed distally of the second segment and disposed at an angle relative to the central longitudinal axis,
   wherein the electrical contact is configured to communicate with the electronic component of the loading unit when the surgical instrument is engaged with the loading unit.

2. The surgical instrument according to claim 1, wherein at least a portion of the first segment of the electrical contact is parallel to the central longitudinal axis.

3. The surgical instrument according to claim 2, wherein at least a portion of the second segment is parallel to the central longitudinal axis.

4. The surgical instrument according to claim 1, wherein the electrical contact is made from sheet metal.

5. The surgical instrument according to claim 1, further including at least one of a processor or a storage unit disposed in electrical communication with the electrical contact.

6. The surgical instrument according to claim 1, wherein the third segment of the electrical contact is disposed at an angle with respect to the first segment.

7. The surgical instrument according to claim 6, wherein at least a portion of the first segment is parallel to at least a portion of the second segment.

8. The surgical instrument according to claim 6, wherein at least a portion of the first segment, and at least a portion of the second segment are parallel to the central longitudinal axis.

9. The surgical instrument according to claim 1, wherein the third segment of the electrical contact is linear.

10. A surgical instrument configured to releasably engage a loading unit having an electronic component, the surgical instrument comprising:
    an elongated portion defining a central longitudinal axis, and including an outer wall; and
    an electrical contact disposed within the outer wall of the elongated portion, at least a portion of the electrical contact being movable radially inward and outward relative to the central longitudinal axis, the electrical contact having at least three segments including a first segment, a second segment, and a third segment, the second segment disposed distally of and radially inward from the first segment, the second segment disposed at an angle relative to the central longitudinal axis, and the third segment disposed distally of the second segment,
    wherein the electrical contact is configured to communicate with the electronic component of the loading unit when the surgical instrument is engaged with the loading unit.

11. The surgical instrument according to claim 10, wherein at least a portion of the first segment of the electrical contact is parallel to the central longitudinal axis.

12. The surgical instrument according to claim 11, wherein at least a portion of the third segment is parallel to the central longitudinal axis.

13. The surgical instrument according to claim 10, wherein the electrical contact is made from sheet metal.

14. The surgical instrument according to claim 10, further including at least one of a processor or a storage unit disposed in electrical communication with the electrical contact.

15. The surgical instrument according to claim 10, wherein the third segment of the electrical contact is parallel to the first segment.

16. The surgical instrument according to claim 10, wherein the second segment of the electrical contact interconnects the first segment and the third segment.

17. The surgical instrument according to claim 10, wherein the third segment of the electrical contact is linear.

18. The surgical instrument according to claim 10, wherein the at least three segments of the electrical contact includes a fourth segment, the fourth segment disposed distally of the third segment.

19. The surgical instrument according to claim 18, wherein a distal portion of the fourth segment of the electrical contact is positioned radially outward from a proximal portion of the fourth segment.

20. The surgical instrument according to claim 19, wherein a distal portion of the second segment of the electrical contact is positioned radially inward from a proximal portion of the second segment.

* * * * *